(12) United States Patent
Mi et al.

(10) Patent No.: US 8,068,909 B2
(45) Date of Patent: Nov. 29, 2011

(54) MEASUREMENT OF CARDIAC PERFORMANCE WITH MOVEMENT SENSORS AND RELATED METHODS

(75) Inventors: Bin Mi, Plymouth, MN (US); Yongxing Zhang, Maple Grove, MN (US); Yunlong Zhang, Mounds View, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 255 days.

(21) Appl. No.: 11/769,402

(22) Filed: Jun. 27, 2007

(65) Prior Publication Data

US 2009/0005829 A1  Jan. 1, 2009

(51) Int. Cl.
*A61B 5/02* (2006.01)
(52) U.S. Cl. ............... 607/17; 607/18; 607/19; 600/515; 600/526
(58) Field of Classification Search ............... 607/17–19; 600/515, 526
See application file for complete search history.

(56) References Cited

U.S. PATENT DOCUMENTS

| | | | |
|---|---|---|---|
| 3,815,611 A * | 6/1974 | Denniston, III | .................... 607/8 |
| 5,157,372 A | 10/1992 | Langford | |
| 5,184,615 A | 2/1993 | Napphloz et al. | |
| 5,280,792 A | 1/1994 | Leong et al. | |
| 5,583,476 A | 12/1996 | Langford | |
| 5,593,430 A * | 1/1997 | Renger | ........................... 607/18 |
| 6,115,633 A | 9/2000 | Lang et al. | |
| 6,477,406 B1 | 11/2002 | Turcott | |
| 2006/0217793 A1* | 9/2006 | Costello | ........................ 607/122 |
| 2008/0021336 A1* | 1/2008 | Dobak, III | .................... 600/508 |
| 2008/0255629 A1* | 10/2008 | Jenson et al. | ................... 607/19 |

FOREIGN PATENT DOCUMENTS

| | | |
|---|---|---|
| WO | WO-00/09012 | 2/2000 |
| WO | WO 2006050385 A2 * | 5/2006 |

OTHER PUBLICATIONS

Hoeland, K et al., "New sensor based on fibre optics for measurement of heart movement", *Med. Biol. Eng. Comput.*, (2002),40:571-575.

(Continued)

*Primary Examiner* — Carl H Layno
*Assistant Examiner* — Deborah Malamud
(74) *Attorney, Agent, or Firm* — Pauly, DeVries Smith & Deffner, L.L.C.

(57) ABSTRACT

Embodiments of the invention are related to implantable devices including movement sensors and related methods for measuring cardiac performance, amongst other things. In an embodiment, the invention includes an implantable electrical stimulation lead. The electrical stimulation lead can include a lead body having a proximal end and a distal end and a sheath defining a central lumen. The lead body can further include an electrical conductor disposed within the central lumen of the sheath. The stimulation lead can further include a stimulation electrode positioned at the distal end of the lead body, the stimulation electrode in electrical communication with the electrical conductor. The electrical stimulation lead can include an flexion sensor coupled to the lead body, the movement sensor configured to generate a signal in response to movement of the lead body. In an embodiment, the invention includes a method of monitoring the condition of a heart failure patient. In an embodiment, the invention includes a method of treating unstable arrhythmia in a patient. Other embodiments are also included herein.

20 Claims, 12 Drawing Sheets

OTHER PUBLICATIONS

Kloppe, A et al., "Mechanical and optical characteristics of a new fiber optical system used for cardiac contraction measurement", *Medical Engineering& Phsyics*, (2004),26:687-694.

Muller, Stefan et al., "Measurement of the Left-ventricular Stroke-volume with a Fiberoptic Sensor", *Automatisierungtechnik (Automatic Control Engineering)*, (Jun. 2004),52:264-269.

Muller, Stefan et al., "A Fiber Optic Sensor System for Control of rate-adaptive cardiac pacemakers and implantable defibrillators", *Biomed Tech*, (2006),51:331-336.

Muller, S et al., "A Fiberoptic Sensor System for Cardiac Monitoring and Electrotherapy", *Biomed. Technik*, (2004),49:311-315.

Muller, S et al., "Fiberoptic Measurement of Myocardial Contraction—Correlation of the Signal with Hemodynamic Values", *BioMed Tech*, (2002),47 Suppl 1 Pt 2:527-529 (Abstract).

Final Office Action mailed Feb. 2, 2011 in co-pending U.S. Appl. No. 11/842,565(our file 115.0033US01), "Implantable Leads With Topographic Features for Cellular Modulation and Related Methods," (12 pages).

\* cited by examiner

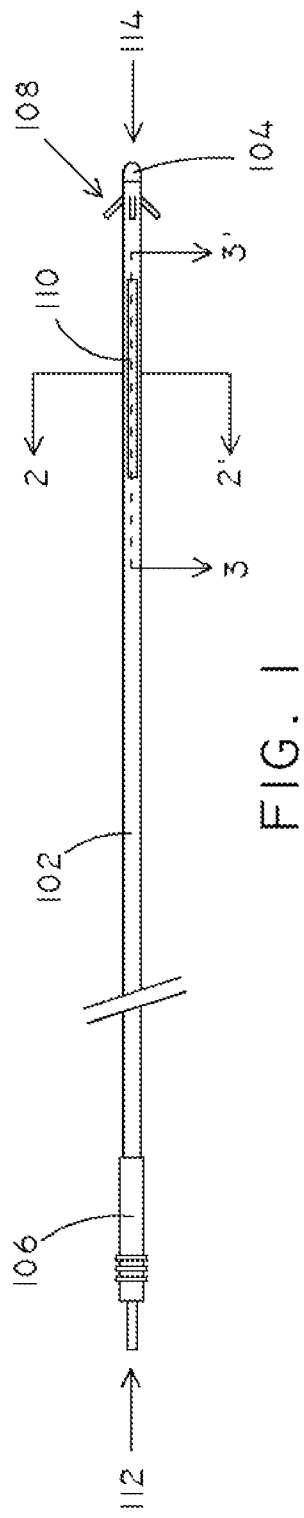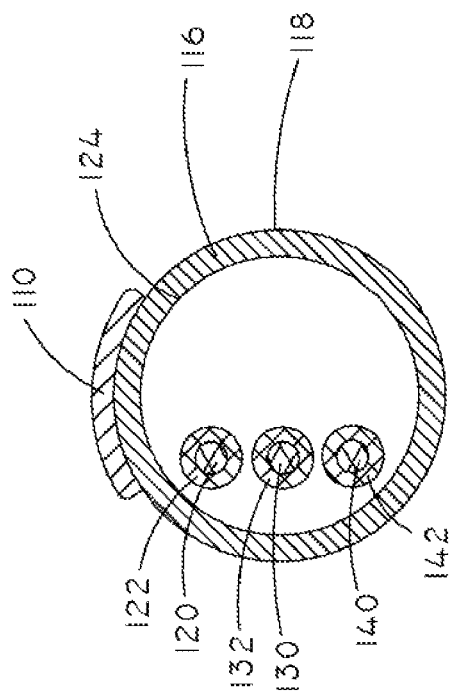

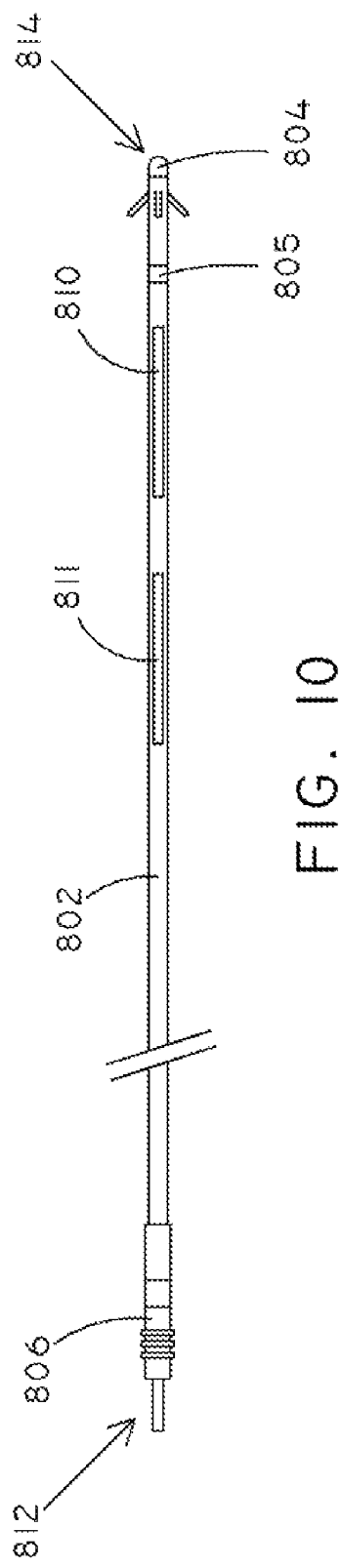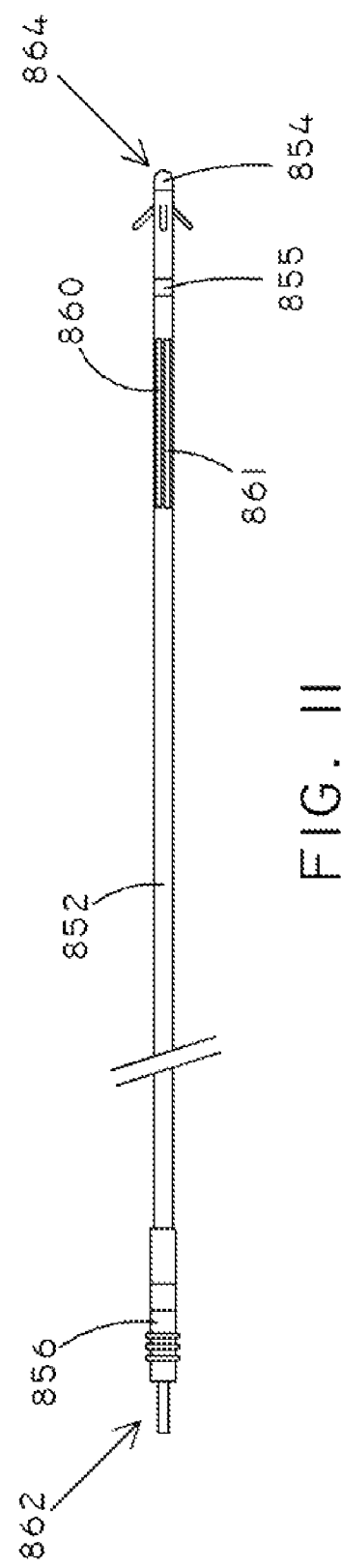

MEASUREMENT OF CARDIAC PERFORMANCE WITH MOVEMENT SENSORS AND RELATED METHODS

TECHNICAL FIELD

This disclosure relates generally to implantable devices and methods for measuring cardiac performance and, more particularly, to implantable devices including movement sensors and related methods for measuring cardiac performance, amongst other things.

BACKGROUND OF THE INVENTION

Cardiopulmonary diseases afflict millions of people each year. In particular, diseases of the heart remain the leading cause of death in the United States. Monitoring patients' physiological state is an important aspect in the diagnosis, management and treatment of various diseases and disorders, including cardiopulmonary diseases. For this reason, significant efforts have been directed at improving monitoring and detection technologies. In specific, significant efforts have been directed at improving monitoring and detection technologies for cardiopulmonary diseases and related diseases that affect cardiopulmonary parameters.

Implantable medical devices can be advantageous as monitoring devices because the monitoring can be performed as desired, without regard to the physical location of the patient. In addition, the use of implantable medical devices for patient monitoring eliminates problems associated with patient compliance. However, many existing techniques for monitoring patients' physiological state fail to adequately assess all of the parameters desired. For example, cardiac output and related measures such as stroke volume are clinically important but difficult to accurately assess with current implantable systems.

For at least these reasons, a need remains for implantable devices and methods for measuring cardiac performance.

SUMMARY OF THE INVENTION

Embodiments of the invention are related to implantable devices including movement sensors and related methods for measuring cardiac performance, amongst other things. In an embodiment, the invention includes an implantable electrical stimulation lead including a lead body having a proximal end and a distal end, the lead body comprising a sheath defining a central lumen and an electrical conductor disposed within the central lumen of the sheath. The implantable electrical stimulation lead further includes a stimulation electrode positioned at the distal end of the lead body, the stimulation electrode in electrical communication with the electrical conductor and a first flexion sensor coupled to the lead body at a point closer to the distal end than the proximal end, the first flexion sensor configured to generate an electrical signal in response to flexion of the lead body.

In an embodiment, the invention includes a method of monitoring the condition of a heart failure patient. The method can include chronically implanting a movement sensor within a subject, the movement sensor configured to produce a first signal in response to movement of cardiac tissue. The method can also include trending the first signal over time and analyzing the first signal trend to identify a pattern showing a sustained reduction in cardiac output.

In an embodiment, the invention includes a method of treating unstable arrhythmia in a patient. The method can include chronically implanting a first sensor within a subject, the first sensor configured to produce a first signal in response to movement of a ventricle, the first sensor comprising a flexion sensor. The method can also include chronically implanting a second sensor within a subject, the second sensor configured to produce a second signal in response to electrical activity of cardiac tissue. The method can also include identifying a pattern in the first signal and/or the second signal indicative of unstable arrhythmia. The method can also include delivering electrical stimulation therapy effective to treat unstable arrhythmia when a pattern is identified indicative of unstable arrhythmia.

In an embodiment, the invention can include a method of diagnosing a hemodynamic problem. The method can include chronically implanting a flexion sensor within a subject; the flexion sensor configured to produce a ventricular movement signal in response to movement of a ventricle. The method can include monitoring the ventricular movement signal for abnormalities during systole. The method can also include monitoring the ventricular movement signal for abnormalities during diastole and the categorizing the hemodynamic problem based on a comparison of the ventricular movement signal during systole versus during diastole.

In an embodiment, the invention can include a method of monitoring right ventricle and left ventricle synchrony including chronically implanting a first movement sensor within a subject, the first movement sensor configured to produce a first signal in response to movement of a right ventricle. The method can also include chronically implanting a second movement sensor within a subject, the second movement sensor configured to produce a second signal in response to movement of a left ventricle. The method can also include processing the first signal and the second signal in order to determine the relative timing of right ventricular contraction versus left ventricular contraction.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which:

FIG. 1 is a schematic view of a stimulation lead in accordance with an embodiment of the invention.

FIG. 2 is a cross-sectional schematic view of a stimulation lead as taken along line 2-2' of FIG. 1.

FIG. 10 is a schematic view of a stimulation lead in accordance with another embodiment of the invention.

FIG. 11 is a schematic view of a stimulation lead in accordance with another embodiment of the invention.

Figure 3:
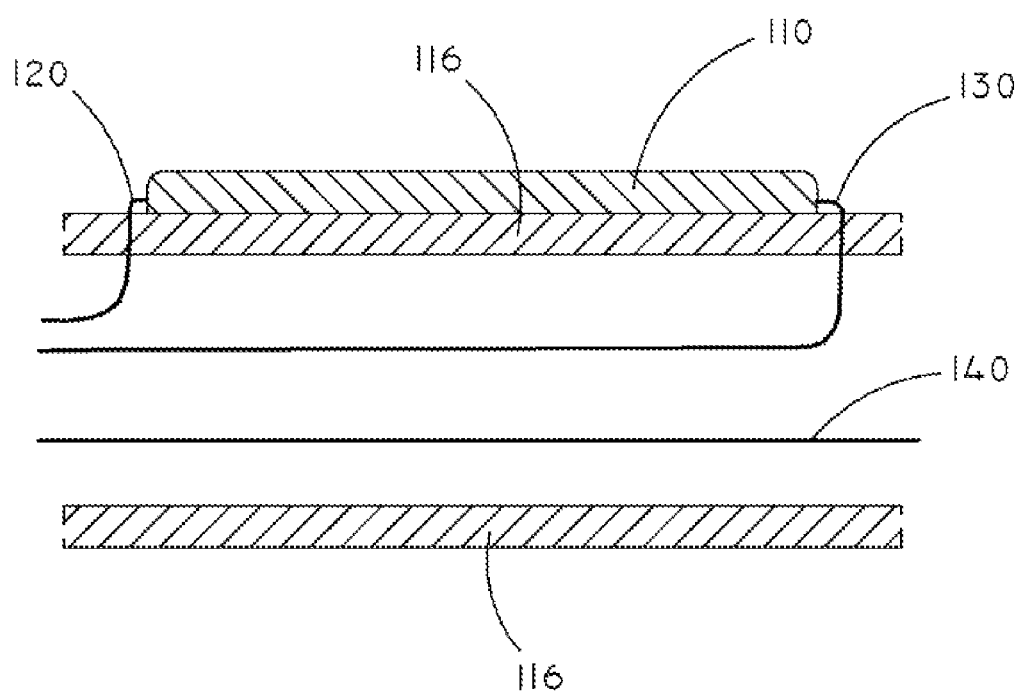
FIG. 3 is a cross-sectional schematic view of a stimulation lead as taken along line 3-3' of FIG. 1.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Embodiments of the invention include implantable devices including movement sensors and related methods for measuring cardiac performance, amongst other things. Movement sensors can be used to detect movement of cardiac tissue in order to detect the physiological state of a patient. Movement sensors can specifically be used to assess cardiac output and related measures such as stroke volume. While not intending to be bound by theory, it is believed that the use of movement sensors to assess cardiac performance can offer advantages over other techniques because of the direct relationship between movement of cardiac tissue during the cardiac contraction cycle and the resulting cardiac output. This direct relationship is believed to result in a desired level of accuracy and reliability in assessing cardiac performance.

As used herein, "movement" refers to movement of a tissue, such as cardiac tissue, with respect to the rest of the body and not movement of the whole body itself, such as the patient moving from one place to another. As such, the term "movement sensor" as used herein refers to a sensor that can measure the movement of a tissue with respect to other tissues of the body. Movement data can be analyzed by itself, or in combination with data from other sensors, in order to accurately gauge a patient's condition. It will be appreciated that movement sensors can be positioned by themselves or can be coupled to a stimulation lead, or other medical device, and inserted into a desired position.

Referring now to FIG. 1, a schematic view of a stimulation lead is shown in accordance with an embodiment of the invention. The stimulation lead includes a lead body 102 with a proximal end 112 and a distal end 114. The stimulation lead includes a stimulation electrode 104 positioned at the distal end 114. In some embodiments, the stimulation lead includes a first electrode, referred to as a tip electrode, and a second electrode, referred to as a ring electrode, disposed a short distance away. It will be appreciated that the stimulation lead can be a pacing lead, defibrillating lead, a coronary venous lead, or the like. In some embodiments, such as where the stimulation lead is to be used for defibrillation in addition to pacing, the stimulation lead can also include a shocking coil near the distal end 114 of the stimulation lead.

The stimulation lead further includes a connection plug 106 for connecting the stimulation lead to an implantable device, such as a cardiac rhythm management (CRM) device. The connection plug 106 can be compatible with various standards for lead-header interface design including the DF-1, VS-1, IS-1 and IS-4 standards. The connection plug 106 can include multiple electrical contacts corresponding to different conductors within the stimulation lead. The stimulation lead can include a fixation element 108 in order to aid in engaging the stimulation lead with target tissue for stimulation, such as cardiac tissue.

A movement sensor 110 can be disposed on the lead body 102. The movement sensor 110 can be configured to generate a signal that is correlated to movement of the lead body 102 in the area of the movement sensor 110. In an embodiment, the movement sensor 110 can be coupled to the lead body at a point closer to the distal end of the stimulation lead than the proximal end of the stimulation lead. In an embodiment, the movement sensor 110 is a flexion sensor. The flexion sensor can be configured to generate a signal in response to flexion, including an electrical and/or an optical signal. Further aspects of exemplary flexion sensors are described in greater detail below.

It will be appreciated that tissues of the heart exhibit a significant degree of movement as various chambers contract and then relax during the cardiac contraction cycle. Such movement can be manifested as displacement, change in a radius of curvature, torsion, and/or rotation, depending on the frame of reference. For example, as the left ventricle contracts or fills with blood, the radius of curvature and torsion of the left ventricle wall is changing. When a movement sensor is disposed in an appropriate position, these changes can be captured as a signal corresponding to movement of the heart.

Movement and/or flexion signals can be processed in order to derive various information regarding cardiac performance. For example, movement and/or flexion signals can be processed in order to derive measures such as the magnitude or degree of movement or flexion exhibited (or displacement), the maximum or average velocity of movement or flexion (during the systolic phase and/or the diastolic phase), the maximum or average acceleration of movement or flexion, and the like. These measures, in turn, can be used as a surrogate index in order to estimate stroke volume and/or cardiac output or changes in stroke volume and/or cardiac output. It will be appreciated that cardiac output can be set as equal to the product of stroke volume and heart rate.

FIG. 2 is a cross-sectional schematic view of a stimulation lead as taken along line 2-2' of FIG. 1. The stimulation lead includes a sheath member 116 with an inner surface 124 and an outer surface 118. The sheath member 116 can be flexible and can be configured to protect other components disposed within the lumen of the sheath member 116. The sheath member 116 can include various biocompatible materials such as polysiloxanes, polyethylenes, polyamides, and the like.

A conductor 120 (not to scale) can be disposed within the lumen of the sheath member 116. The conductor 120 can be an electrical conductor. The conductor 120 can include various materials including copper, aluminum, silver, gold, and various alloys such as tantalum/platinum, MP35N and the like. An insulator 122 can surround the conductor 120. The insulator 122 can include various materials such as electrically insulating polymers. In some embodiments, the conductor 120 is configured as a coil. Multiple conductors can be disposed within the lumen of the sheath member 116. For example, the stimulation lead can also include conductors 130 and 140, surrounded by insulators 132 and 142 respectively. One or more of the conductors can be in communication with movement sensor 110. In embodiments with multiple stimulation electrodes, separate conductors can be in communication with each stimulation electrode of the stimulation lead. In some embodiments, one or more of the conductors can be optical conductors, such as an optical fiber.

In this embodiment, the movement sensor 110 is disposed on the outside surface 118 of the sheath member 116. As the sheath member 116 moves, the movement sensor 110 also moves and generates a signal corresponding to that movement. While the movement sensor 110 of FIG. 2 covers only a small portion of the outer surface 118 of the stimulation lead, it will be appreciated that movement sensor 110 can be configured to cover any amount of the sheath member 116 desired.

Referring now to FIG. 3, a schematic cross-sectional view of a portion of a stimulation lead is shown as taken along line 3-3' of FIG. 1. The stimulation lead includes sheath member 116 and movement sensor 110 disposed on the sheath member 116. Conductors 120 and 130 are in electrical communication with movement sensor 110. As shown in FIG. 3, conductors 120 and 130 pass through the lumen of the stimulation lead and then through the sheath member 116 in order to connect to the movement sensor 110. However, in other embodiments, conductors 120 and 130 can be disposed on the outside of sheath member 116 and not pass through the lumen of the stimulation lead. Conductor 140 also passes through the lumen of the stimulation lead.

Figure 4:
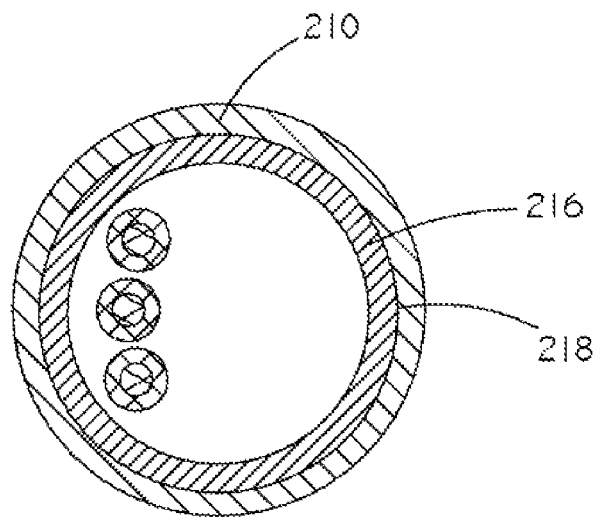
FIG. 4 is a cross-sectional schematic view of a stimulation lead in accordance with another embodiment of the invention.

Referring now to FIG. 4, a cross-sectional view is shown of a stimulation lead in accordance with another embodiment of the invention. The stimulation lead includes a sheath 216 with an exterior surface 218. The stimulation lead further includes a movement sensor 210 completely surrounding the exterior surface 218 of sheath member 216.

Figure 5:
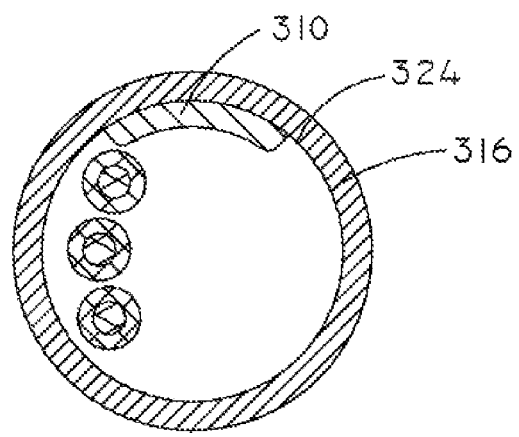
FIG. 5 is a cross-sectional schematic view of a stimulation lead in accordance with another embodiment of the invention.

In some embodiments, the movement sensor can be disposed on the inside of the sheath. Referring now to FIG. 5, a cross-sectional view of a stimulation lead is shown in accordance with another embodiment of the invention. The stimulation lead includes a sheath member 316 with an inner surface 324. In this embodiment, the movement sensor 310 is disposed on the inside surface 324 of the sheath member 316. It is believed that this configuration can provide an advantage in that the movement sensor 310 is protected by the sheath member 316.

Figure 6:
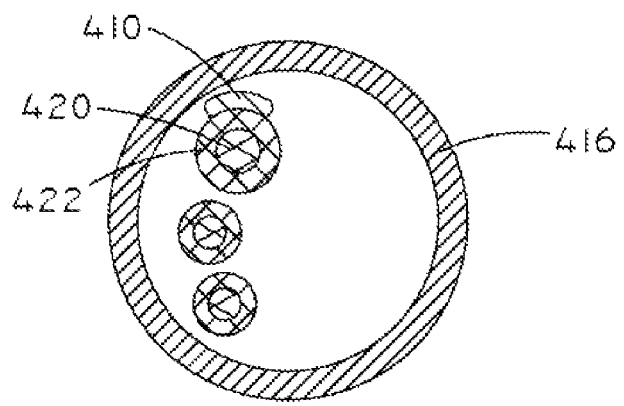
FIG. 6 is a cross-sectional schematic view of a stimulation lead in accordance with another embodiment of the invention.

It will be appreciated that there are many different possibilities with respect to where the movement sensor can be disposed on the stimulation lead. In some embodiments, the movement sensor can be disposed over a conductor within the lumen of stimulation lead body. Referring now to FIG. 6, a cross-sectional view of a stimulation lead is shown in accordance with another embodiment of the invention. The stimulation lead includes a sheath member 416. A conductor 420 can be disposed within the lumen of the sheath member 416. An insulator 422 can surround the conductor 420. In this embodiment, the movement sensor 410 is disposed on the surface of the insulator 422. In some embodiments, the movement sensor 410 is disposed between the insulator 422 and the conductor 420. In some embodiments, the movement sensor 410 is disposed within the lumen of the sheath, but is separate from other components within the lumen, such as the conductor 420.

Various types of movement sensors can be used with embodiments of the invention. By way of example, the movement sensor can be a flexion sensor. In some embodiments, the flexion sensor generates an optical signal in response to flexion. In other embodiments, the flexion sensor generates an electrical signal in response to flexion. The electrical signal can be in the form of a current, a voltage, a resistance, or changes in the same. For example, the flexion sensor can be configured so that its resistance varies as a function of bending of the sensor. An exemplary electrical flexion sensor is described in U.S. Pat. No. 5,583,476, the content of which is herein incorporated by reference. An exemplary electrical flexion sensor is commercially available from Flexpoint Sensor Systems, Inc., Draper, Utah. In other embodiments, the flexion sensor can include a piezoelectric element that generates a current in response to bending of the flexion sensor.

Figure 7:
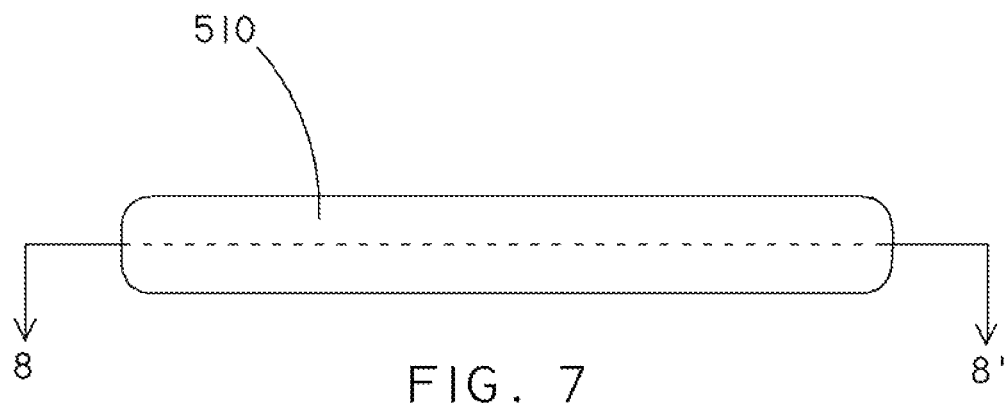
FIG. 7 is a top schematic view of a flexion sensor in accordance with an embodiment of the invention.
Figure 8:
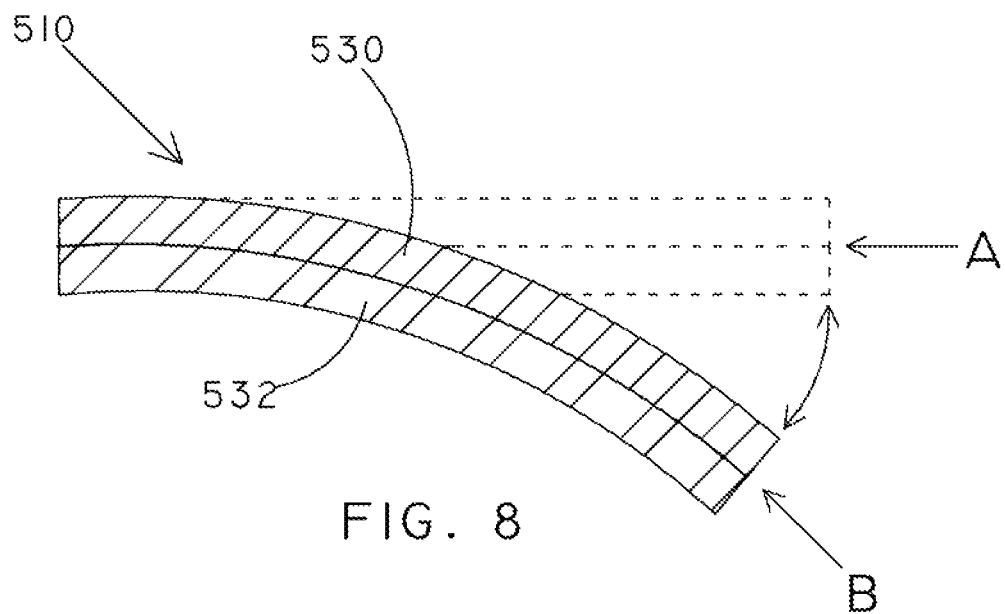
FIG. 8 is a cross-sectional schematic view of a flexion sensor as taken along line 8-8' of FIG. 7.

Referring now to FIG. 7, a top schematic view is shown of an exemplary flexion sensor 510 in accordance with an embodiment of the invention. FIG. 8 shows a cross-sectional view of the flexion sensor 510 as taken along line 8-8' of FIG. 7. The flexion sensor 510 includes a substrate 532 and a conductive material layer 530 disposed over the substrate 532. In some embodiments, the substrate 532 is made from a flexible material, such as a polyamide. The conductive material layer 530 can be configured so that its resistance changes with the degree to which the conductive material layer 530 is flexed. For example, the flexion sensor 510 can assume a first position A and then flex in order to assume a second position B. The resistance of the conductive material layer 530 changes in a manner so as to allow the degree of flexion to be calculated. The conductive material layer 530 can include graphite in combination with a binder.

In some embodiments, the substrate 532 is part of a stimulation lead, such as a sheath or an insulator. For example, the conductive material layer 530 can be applied directly onto a portion of the stimulation lead, such as directly onto the sheath on the inside or outside surface. For example, the material of the conductive material layer 530 can be printed, sprayed, or brushed on to a surface of the stimulation lead.

While not intending to be bound by theory, it is believed that electrical flexion sensors can be advantageous because they can be made relatively thin and therefore easily accommodated in conjunction with various types of electrical stimulation leads. A thin profile is desirable because electrical stimulation leads are frequently threaded through vasculature into the heart. In addition, a thin configuration of the flexion sensor is desirable because it is less likely to render the portion of the stimulation lead onto which it is disposed undesirably stiff. In some embodiments, the thickness of the conductive material layer 530 in combination with the substrate 532 is less than about 0.5 mm. In some embodiments, the thickness of the conductive material layer 530 in combination with the substrate 532 is less than about 0.25 mm. In some embodiments, the thickness of the conductive material layer 530 in combination with the substrate 532 is less than about 0.1 mm.

It will be appreciated that in various embodiments the flexion sensor can take on various shapes and configurations. In some embodiments, the flexion sensor can include a layered configuration. In other embodiments, the flexion sensor can include a coiled configuration, a wrapped configuration, a straight configuration, and the like.

Figure 9:
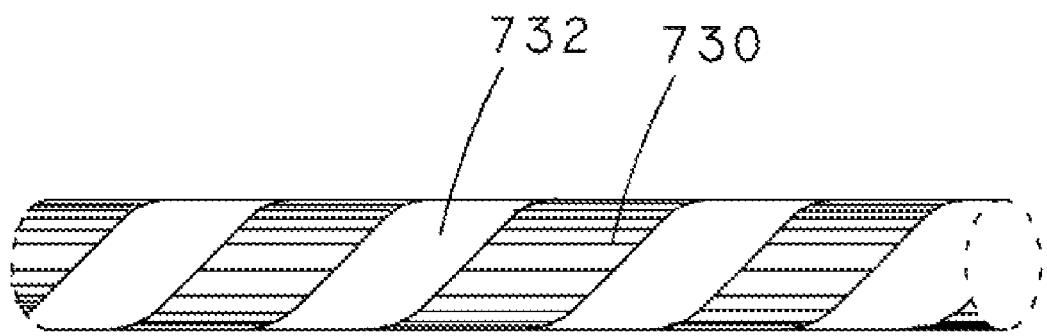
FIG. 9 is a schematic perspective view of a flexion sensor disposed on a lead body in accordance with an embodiment of the invention.

Referring now to FIG. 9, a schematic perspective view is shown of a portion of a stimulation lead in accordance with another embodiment of the invention. The stimulation lead includes a sheath 732 and a flexion sensor 730 wrapped around the sheath in a helical (helicoid) pattern. While not intending to be bound by theory, it is believed that a helical pattern can be advantageous as it renders the resulting flexion sensor sensitive to flexion in many different directions, particularly in the context of a flexion sensor that changes resistance based on flexion. It will be appreciated that the flexion sensor can take on many different shapes, including straight or curved lines, helicoids, spirals, and other 2-D or 3-D geometrical patterns, amongst other patterns.

In some embodiments, flexion sensors used in devices and systems herein can be optical flexion sensors. Optical flexion sensors can include an optical conductor such as an optical fiber. Optical fibers generally include a core surrounded by a cladding layer. To confine the optical signal to the core, the refractive index of the core is typically greater than that of the cladding. The boundary between the core and cladding may either be abrupt, in step-index fiber, or gradual, in graded-index fiber. Optical signals can pass through the core of the optical fiber by means of total internal reflection. However, if the angle of incidence of light striking the boundary between the core and cladding exceeds a critical value, then some amount of the optical signal will pass outside of the optical fiber and not be reflected internally. As such, an optical fiber that is bent beyond a critical angle will exhibit some degree of optical signal loss. Therefore, bending of an optical fiber can be detected by monitoring the optical signals transmitted by the optical fiber. In one approach, an optical signal, such as that generated by a light emitting diode (LED), can be passed through an optical conductor, reflected at the tip, passed back through the optical conductor and then received by a component such as a photodiode.

In some embodiments, the optical conductor includes an unmodified optical fiber. However, in some embodiments, portions of the optical fiber cladding can be removed to enhance sensitivity of specific regions of the optical fiber to bending signal loss. In some embodiments, the optical conductor includes a bend-enhanced fiber (BEF) sensor. BEFs can be made by treating optical fibers to have an optically absorptive zone along a thin axial stripe. Light transmission through the fiber past this zone then becomes a robust function of curvature that is more sensitive to bending than otherwise similar untreated optical fiber.

It will be appreciated that embodiments of stimulation leads can include multiple flexion sensors. Referring now to FIG. 10, an embodiment of a stimulation lead is shown in accordance with an embodiment of the invention. The stimulation lead includes a lead body 802 with a proximal end 812 and a distal end 814. The stimulation lead includes a tip electrode 804 positioned at the distal end 814 and a ring electrode 805. As such, this embodiment of a stimulation lead is a bipolar stimulation lead. The stimulation lead further includes a connection plug 806 for connecting the stimulation lead to an implantable device, such as a cardiac rhythm management (CRM) device.

A first movement sensor 810, such as a flexion sensor, can be disposed on the lead body 802. The first movement sensor 810 can be configured to generate a signal that is correlated to the degree to which the lead body 802 flexes in the area of the movement sensor 810. A second movement sensor 811, such as a flexion sensor, can also be disposed on the lead body 802. The second movement sensor 811 can be configured to generate a signal that is correlated to the degree to which the lead body 802 flexes in the area of the second movement sensor 811. First movement sensor 810 and second movement sensor 811 can be positioned on the lead body such that they are in position to measure motion of tissue relevant to monitoring cardiac condition and performance. For example, in some embodiments, first movement sensor 810 can be positioned in order to measure movement of a ventricle and second movement sensor 811 can be positioned in order to measure movement of an atrium.

In some embodiments, multiple flexion sensors can be disposed in parallel for various purposes including providing enhanced accuracy of flexion measurements. Referring now to FIG. 11, an embodiment of a stimulation lead is shown in accordance with an embodiment of the invention. The stimulation lead includes a lead body 852 with a proximal end 862 and a distal end 864. The stimulation lead includes a tip electrode 854 positioned at the distal end 864 and a ring electrode 855. The stimulation lead further includes a connection plug 856 for connecting the stimulation lead to an implantable device, such as a cardiac rhythm management (CRM) device. A first movement sensor 860, such as a flexion sensor, can be disposed on the lead body 852. A second movement sensor 861, such as a flexion sensor, can be disposed on the lead body 852 parallel to the first movement sensor 860.

It will be appreciated that movement sensors on implantable medical devices such as electrical stimulation leads can be positioned in many different places within or around the heart both endocardially and epicardially. In some embodiments, the movement sensor can be disposed on an electrical stimulation lead so that the movement sensor is positioned within areas adjacent to the heart, such as within the pulmonary artery.

The measurement of ventricular motion can be of particular diagnostic value because of its relation to cardiac output. In this regard, both motion of the right ventricle and the left ventricle can be relevant. In an endocardial approach to measuring movement of the right ventricle, a movement sensor can be disposed on a stimulation lead so that the movement sensor is positioned directly into the right ventricle in order to measure movement of the ventricle.

Figure 12:
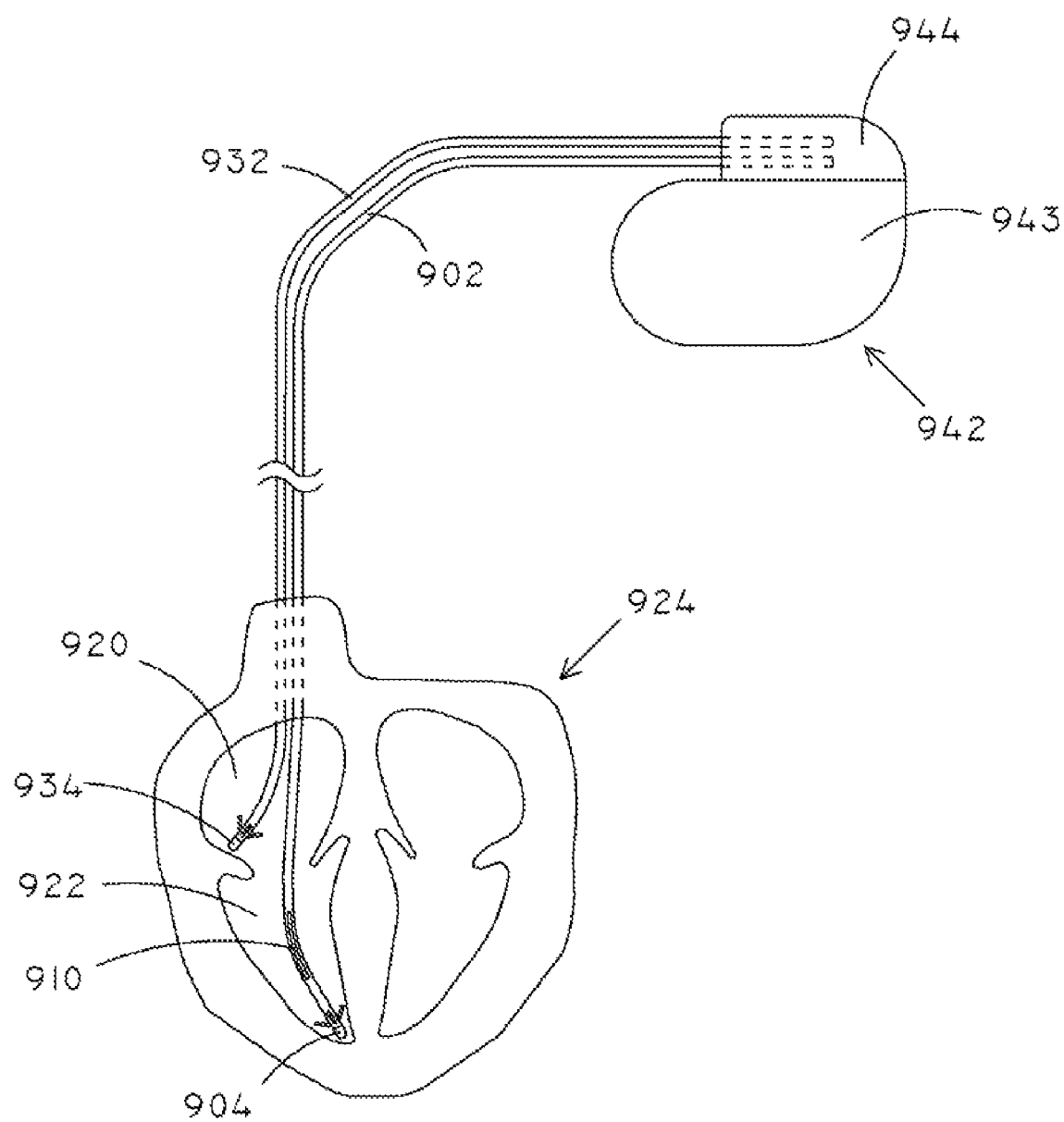
FIG. 12 is a schematic view of an implantable medical system in accordance with an embodiment of the invention.

Referring now to FIG. 12, an embodiment of an implantable system with a movement sensor is shown in accordance with an embodiment of the invention. An implantable medical device 942, such as a CRM device, is coupled to a first stimulation lead 902 and a second stimulation lead 932. The implantable medical device 942 can include a housing 943 and a header 944. Various electrical components, such as a processor, can be disposed within the housing 943. The header 944 can serve to couple the stimulation leads to the housing 943. First stimulation lead 902 includes an electrode 904 that is disposed within the right ventricle 922 of the heart 924. A movement sensor 910 is disposed on the first stimulation lead 902 in a position to detect movement of the right ventricle 922. Second stimulation lead 932 includes an electrode 934 that is disposed within the right atrium 920 of the heart 924.

The implantable medical device 942 can be configured to receive and process the signal from the movement sensor(s). In some embodiments, the implantable medical device 942 can be configured to switch the movement sensor 910 on and off in order to provide a desired measurement frequency while minimizing power consumption. In some embodiments, the implantable medical device 942 can be configured to switch the movement sensor 910 on for a period of time, referred to as a measurement period, and then switch the movement sensor 910 back off. The number of measurement periods in a given period of time (or sampling rate) can be programmed into the implantable medical device 942 by a clinician or care provider through a programmer device or an advanced patient management system.

In some embodiments, the sampling rate can be adjusted by the implantable device according to the current condition of the patient. When the patient is exhibiting signs of an unstable condition, such as an unstable arrhythmia then the sampling rate can be increased. When the patient is in a stable condition, then the sampling rate can be decreased.

While not intending to be bound by theory, it is believed that signals produced by movement sensors during periods of relative inactivity of a patient exhibit reduced variability. As such, in some embodiments, the implantable medical device 942 is configured to initiate measurement periods while the patient is inactive. In some embodiments, patient inactivity can be gauged via a posture sensor. For example, the implantable medical device can include a posture sensor and the implantable medical device can be configured to turn on the movement sensor only when the patient's posture indicates that they are likely inactive, such as lying down. An exemplary posture sensor can include an accelerometer configured to provide an output signal due to the force of gravity which has a polarity and magnitude dependent on the degree to which a sensitive axis is tilted forward or rearward from the direction of earth's gravity. As such, a body posture sensor can be configured to sense a range of angles with respect to the earth's gravity, varying between a zero degree angle associated with lying down and a 90 degree angle associated with standing erect.

In some embodiments, patient inactivity can be presumed based on the time of day. For example, the implantable medical device can include a clock and then the implantable medical device can be configured to turn on the movement sensor only during hours of the day when the patient is likely to be inactive, such as between midnight and 5:00 AM, for example. It will be appreciated that multiple aspects can be combined in order to gauge the activity level of the patient. For example, information from both a posture sensor and a clock can be evaluated before initiating a measurement period.

In some embodiments, movement sensors can be positioned in order to detect movement of the left ventricle. For example, a flexion sensor can be disposed on a stimulation lead that passes directly into the left ventricle. However, some clinicians prefer not to have any device disposed directly within (endocardially) the left ventricle chamber because of the risk of various complications. As such, one approach is to position a stimulation lead within the coronary venous system where movement of the left ventricle is reflected. Because the coronary veins run along the epicardial surface of the heart, they can be an ideal place to measure movement of the heart and, in particular, movement of the left ventricle of the heart.

Figure 13:
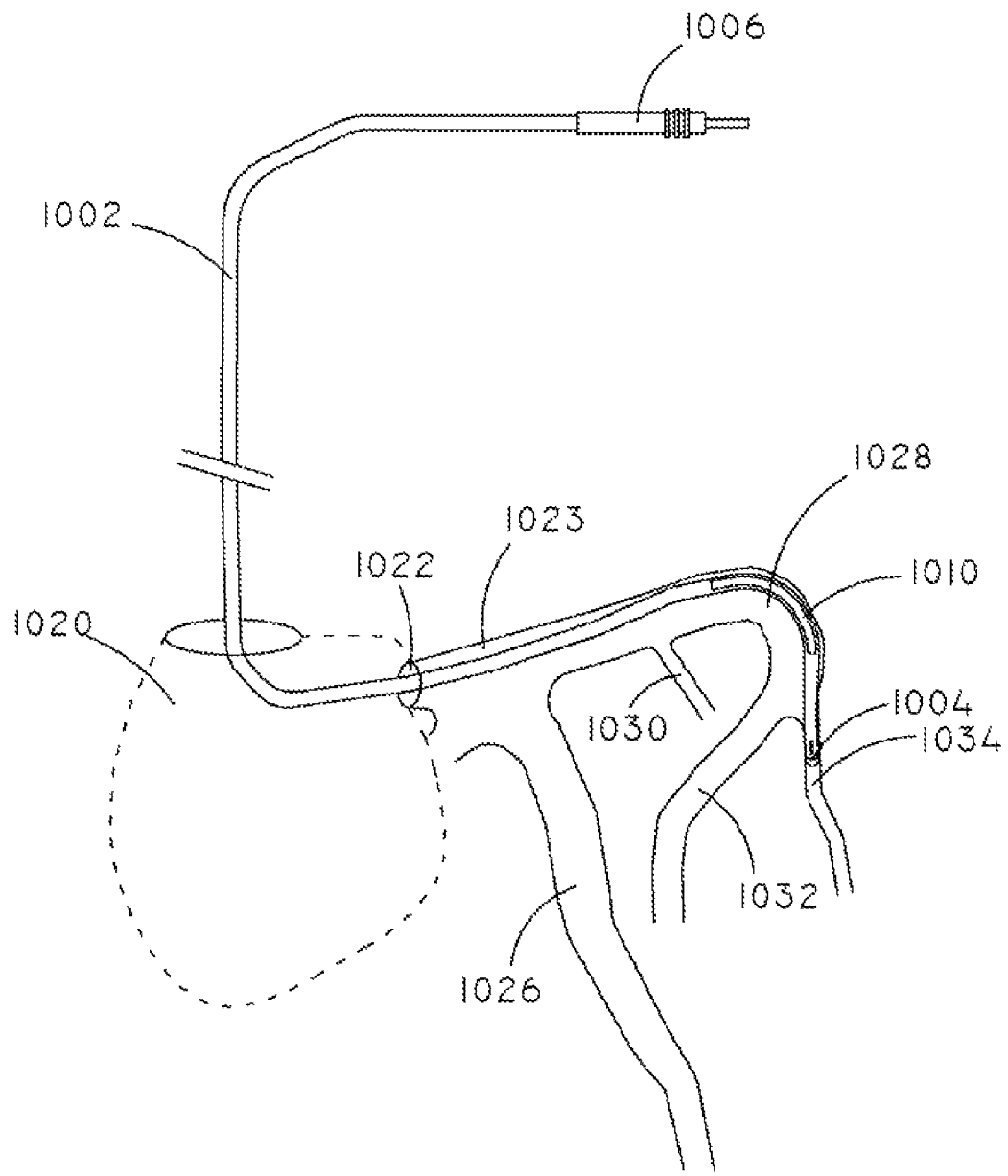
FIG. 13 is a schematic view of a stimulation lead positioned within the coronary venous system in accordance with another embodiment of the invention.

Referring now to FIG. 13, a schematic view is shown of a stimulation lead disposed within the coronary venous system. The stimulation lead includes a lead body 1002 and a connecting plug 1006. The stimulation lead also includes a stimulation electrode 1004 and a flexion sensor 1010. The stimulation lead passes into the heart through the superior vena cava and into the right atrium 1020. The stimulation lead then passes through the coronary sinus ostium 1022 and into the coronary sinus 1023. Tributaries of the coronary venous system include the middle cardiac vein 1026, the great cardiac vein 1028, the posterior vein of the left ventricle 1030, the lateral vein of the left ventricle 1034, and the anterior interventricular vein 1032, amongst others. In this embodiment, the stimulation lead passes through the great cardiac vein 1028 and into the lateral vein of the left ventricle 1034. In this embodiment, the flexion sensor 1010 is positioned so that it can detect motion of the left ventricle. However, it will be appreciated that the stimulation lead can be disposed within various parts of the coronary venous system, such as any of the tributaries outlined above, based on factors such as individual anatomical characteristics and preferences of the clinician.

Figure 14:
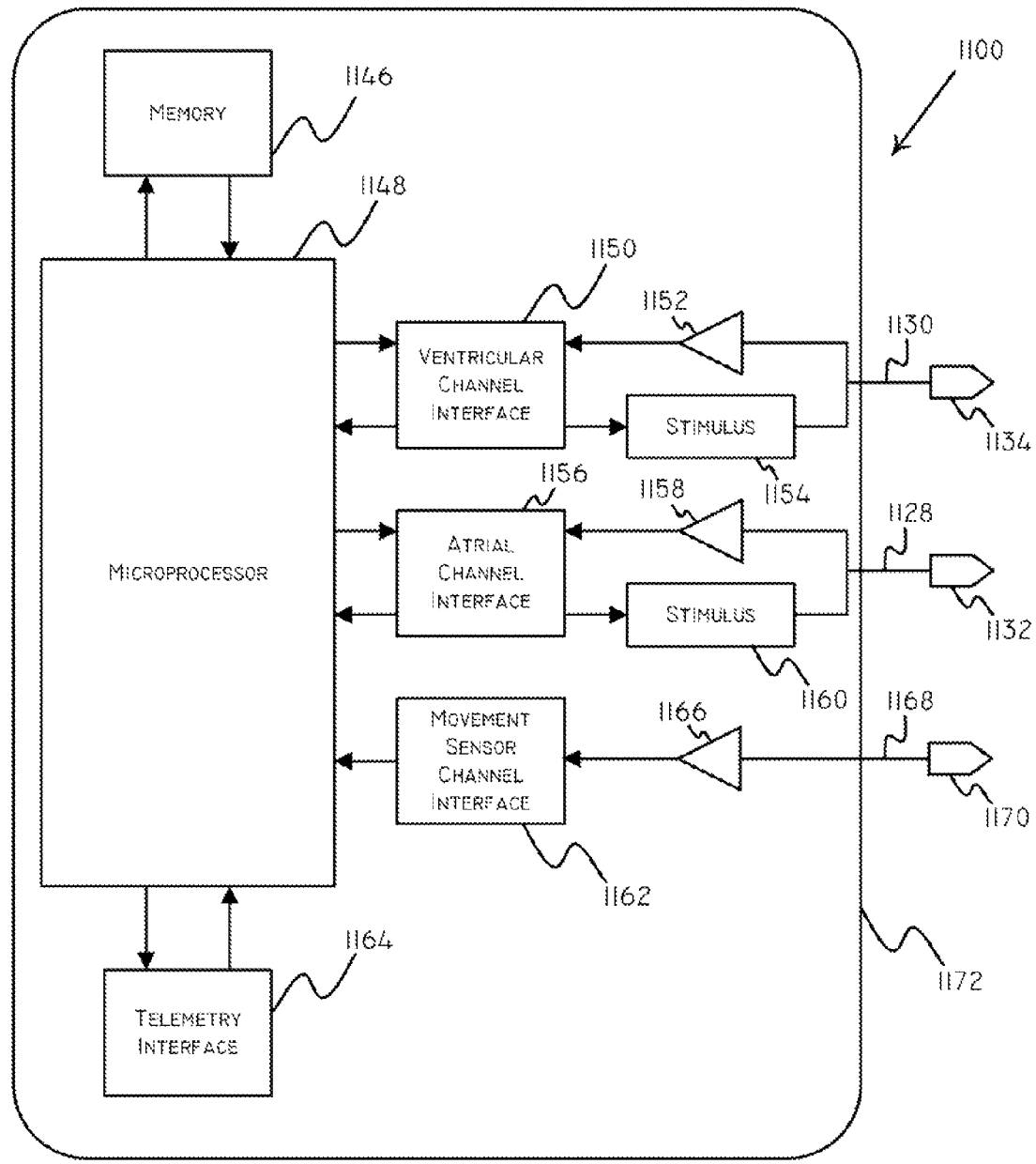
FIG. 14 is a schematic view of components of an implantable medical system in accordance with an embodiment of the invention.

Embodiments of the invention can specifically include implantable systems including an implantable medical device, such as a CRM device, along with one or more electrical stimulation leads, and one or more flexion sensors. Implantable medical devices can specifically include pacemakers, implantable cardioverter-defibrillators (ICDs), cardiac resynchronization therapy (CRT) devices, and the like. Implantable medical devices can include various components in order to receive and process signals from flexion sensors. Referring now to FIG. 14, some components of an exemplary implantable system 1100 are schematically illustrated. The implantable medical system 1100 can include an implantable medical device 1172 coupled to one or more stimulation leads 1130 and 1128. The implantable device 1172 can also be coupled to a movement sensor 1170, such as a flexion sensor, via a conductor 1168 that can provide communication between the movement sensor 1170 and the implantable device 1172.

The implantable device can include a microprocessor 1148 (or processor) that communicates with a memory 1146 via a bidirectional data bus. The memory 1146 typically comprises ROM or RAM for program storage and RAM for data storage. The implantable device can be configured to execute various operations such as processing of signals and execution of methods as described herein. A telemetry interface 1164 is also provided for communicating with an external unit, such as a programmer device or a patient management system.

The implantable device can include ventricular sensing and pacing channels comprising sensing amplifier 1152, output circuit 1154, and a ventricular channel interface 1150 which communicates bidirectionally with a port of microprocessor 1148. The ventricular sensing and pacing channel can be in communication with stimulation lead 1130 and electrode 1134. The implantable device can include atrial sensing and pacing channels comprising sensing amplifier 1158, output circuit 1160, and an atrial channel interface 1156 which communicates bidirectionally with a port of microprocessor 1148. The atrial sensing and pacing channel can be in communication with stimulation lead 1128 and electrode 1132. For each channel, the same lead and electrode can be used for both sensing and pacing. The channel interfaces 1150 and 1156 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

The implantable device can also include a movement sensor channel comprising sensing amplifier 1166 and a movement sensor channel interface 1162 which communicates with a port of microprocessor 1148. The movement sensor channel can be in communication with movement sensor 1170 via conductor 1168. In some embodiments, conductor 1168 is disposed within a stimulation lead, such as stimulation lead 1128 or 1130.

Embodiments of the invention can include various methods that include or rely upon data gathered with the aid of a flexion sensor. Such methods can be usefully applied in many contexts, including in the context of implantable cardioverter defibrillators (ICDs). One function of ICDs is to identify and terminate hemodynamically unstable arrhythmias such as ventricular fibrillation and ventricular tachycardia. The term "unstable" is used to designate those arrhythmias where cardiac output falls to a level insufficient to ensure adequate perfusion of vital organs. As such, hemodynamically unstable arrhythmias stand in contrast to less dangerous arrhythmias such as atrial fibrillation and sinus tachycardia.

Therapy to terminate a hemodynamically unstable arrhythmia can involve delivering a large shock significant enough to cause great discomfort for the patient. As such, there is a need for ICDs to accurately discriminate between hemodynamically unstable arrhythmias that require immediate treatment and other less serious types of arrhythmias. Typically, ICDs discriminate between hemodynamically unstable arrhythmias and other arrhythmias through analysis of the intracardiac electrogram, with features such as heart rate, interval regularity, and QRS morphology. Unfortunately, there are limits to the accuracy of discrimination that can be achieved using only data from intracardiac electrograms. However, reduced cardiac output is a hallmark of hemodynamically unstable arrhythmias and, as such, can be usefully applied in discrimination of the same, either in conjunction with data from an intracardiac electrogram or by itself.

Figure 15:
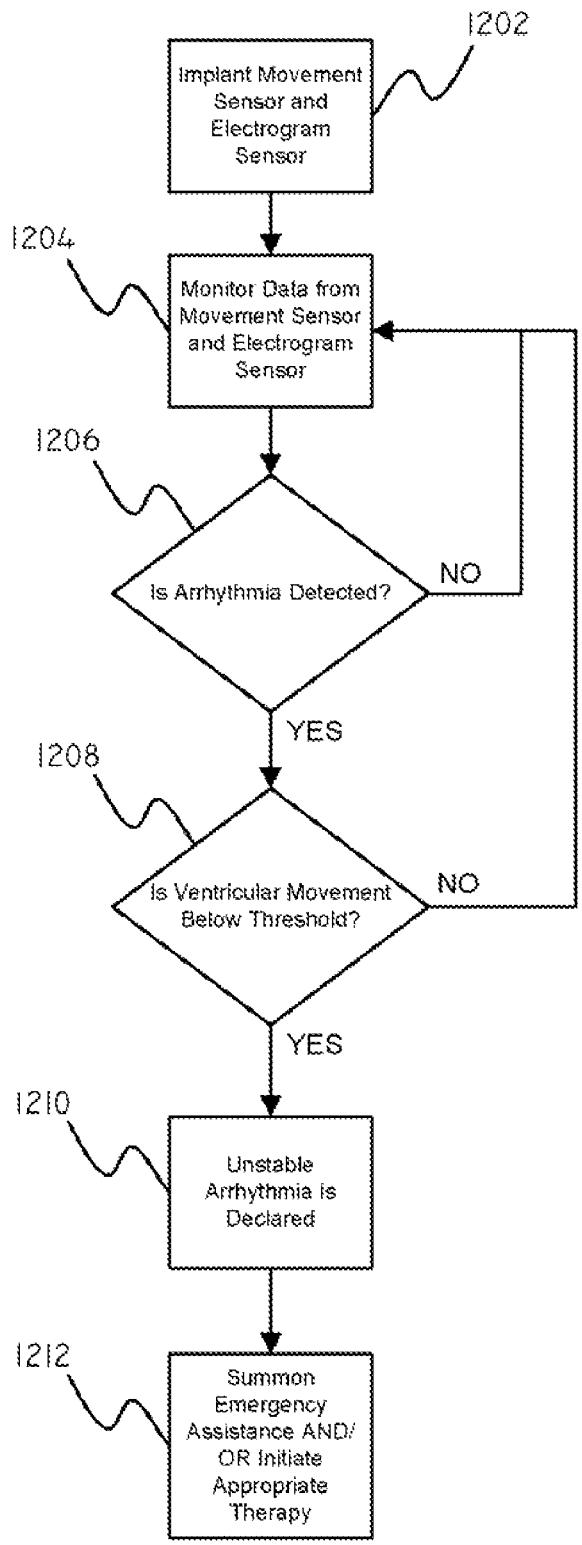
FIG. 15 is a flow chart illustrating operations of a method in accordance with an embodiment of the invention.

Referring now to FIG. 15, a flow chart is shown illustrating a method of identifying a hemodynamically unstable arrhythmia in a patient. In an embodiment, the invention includes an implantable medical device including a processor, the medical device configured to execute operations of a method of identifying a hemodynamically unstable arrhythmia in a patient. In a first operation 1202, a movement sensor and an intracardiac electrogram sensor are implanted in a patient. Such devices can be implanted using standard surgical techniques. In some embodiments, the intracardiac electrogram sensor can be a part of a standard implantable CRM device, such as an ICD. The intracardiac electrogram sensor can use electrical stimulation leads in order to sense electrical activity within the heart. The movement sensor can be disposed on the electrical stimulation leads and positioned so as to produce a signal reflecting movement of one or both of the ventricles. In some embodiments, the movement sensor can be disposed in the body separately from other implanted components and can be configured to transmit a signal wirelessly.

In a second operation 1204, signals from the movement sensor and the intracardiac electrogram sensor are monitored. This can also include recording and analyzing the signal data. In third operation 1206, the system can be configured to evaluate whether or not an arrhythmia is detected. This determination can be made on the basis of the signal from the intracardiac electrogram. Specifically, R-R frequency, R-R interval regularity, and QRS morphology can be assessed in order to determine whether or not the patient is currently exhibiting an arrhythmia. Various techniques for identifying an arrhythmia based on an electrogram signal can be used including such techniques described in U.S. Pat. No. 5,184,615 and U.S. Pat. No. 5,280,792, the contents of both of which are herein incorporated by reference.

Alternatively, the determination of whether or not an arrhythmia is occurring can be based on data from the movement sensor itself. For example, the frequency of oscillations in the movement data corresponding to full or even partial contraction can be used to assess whether or not an abnormal heart rhythm is present.

If an arrhythmia is not detected, then the system can go back to operation 1204 and resume monitoring. However, if an arrhythmia is detected, then the system can go on to evaluate the magnitude of ventricular movement taking place. By definition, cardiac output is reduced during hemodynamically unstable arrhythmias. When cardiac output is reduced, the degree of movement of one or both of the ventricles is reduced. This condition can thus be identified by evaluating the signal from a movement sensor. Therefore, at operation 1208, the system evaluates whether or not the ventricular movement is below a threshold amount. If not, then the system can go back to operation 1204 and resume monitoring. If so, then the presence of a hemodynamically unstable arrhythmia is declared at operation 1210. Finally, at operation 1212, emergency assistance is summoned and/or appropriate therapy is initiated. For example, the system can administer an electrical shock in order to terminate the unstable arrhythmia.

It will be appreciated that there are many different ways of evaluating data from a movement sensor in order to determine whether or not a hemodynamically unstable arrhythmia is taking place. For example, in some embodiments, this evaluation includes determining whether the movement falls below a threshold level, as described with respect to FIG. 15. The threshold can be input into the system by a care provider through an external device such as a programmer. Alternatively, the threshold can be set as some percentage of normal values for a specific patient. For example, the system can monitor average ventricular movement over a period of time and then set the threshold at some percentage of this average. It will be appreciated that many different approaches can be used.

Figure 16:
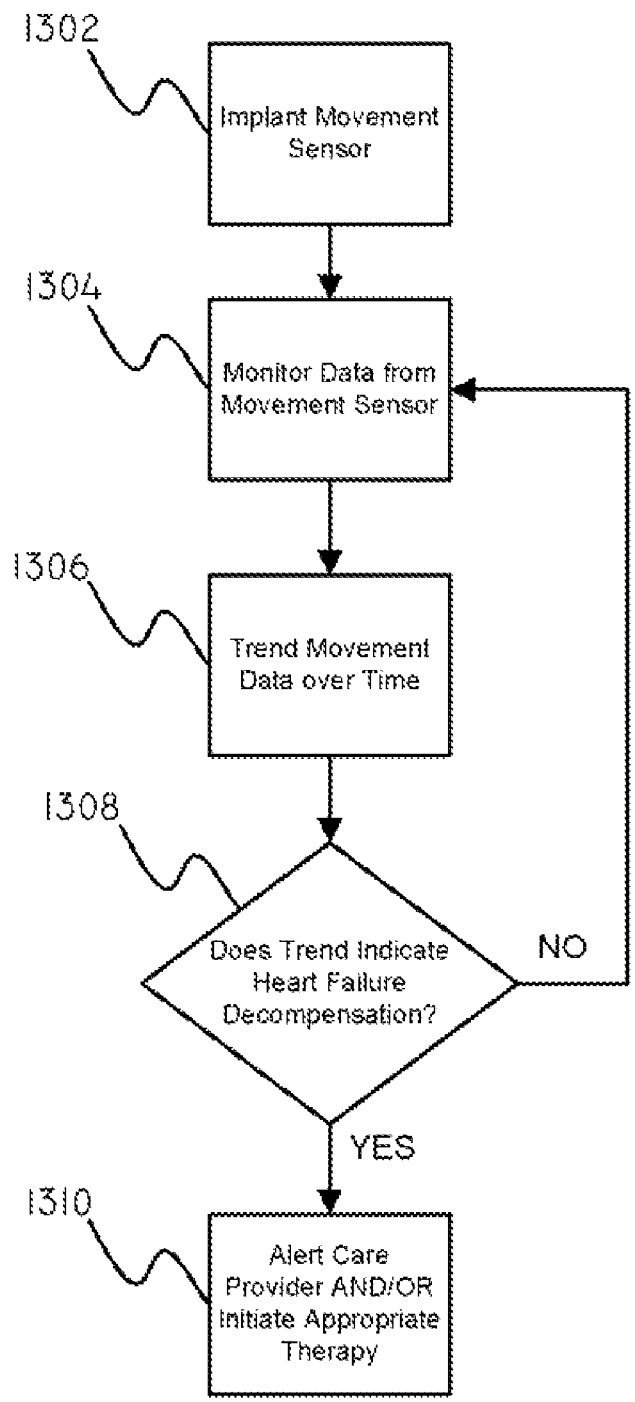
FIG. 16 is a flow chart illustrating operations of a method in accordance with another embodiment of the invention.

Reduced cardiac output is also a hallmark of heart failure decompensation and, as such, can be usefully applied in monitoring the condition of heart failure patients. Referring now to FIG. 16, a flow chart is shown illustrating a method monitoring the condition of a heart failure patient. In an embodiment, the invention includes an implantable medical device including a processor, the medical device configured to execute operations of a method of monitoring the condition of a heart failure patient. In a first operation 1302, a movement sensor is implanted in a patient. In a second operation 1304, data from the movement sensor is monitored. In a third operation 1306, data from the movement sensor is trended over time. In a fourth operation 1308, the trend is evaluated in order to determine whether or not it indicates that heart failure decompensation is taking place. Heart failure decompensation will generally be reflected by a trend showing cardiac output steadily declining with time. As such if the signal from the movement sensor shows that movement is steadily declining with time, then this is a trend indicative of heart failure decompensation. If heart failure decompensation is not taking place, then the system goes back to monitoring at operation 1304. However, if heart failure decompensation is indicated, then at operation 1310, the system can alert a care provider and/or can initiate appropriate therapy. Appropriate therapy can include initiation or modulation of electrical stimulation therapy. Appropriate therapy can also include administration of various active agents.

Analysis of movement data of the heart can also be useful for purposes of monitoring and responding to the degree of synchrony between the right ventricle and the left ventricle. In a heart that is operating normally, the right and left ventricles contract simultaneously. However, in some disease states, the right or left ventricle may contract before the other. In addition, in some circumstances where both the right and left ventricle are being paced, the right or left ventricle may contract before the other due to particulars of device implantation such as the specific lead placement. An asynchronous state of contraction can lead to a reduction in the pumping efficiency of the heart. As such, it can be desirable to indentify such an asynchronous state and take appropriate action to re-establish synchrony.

Figure 17:
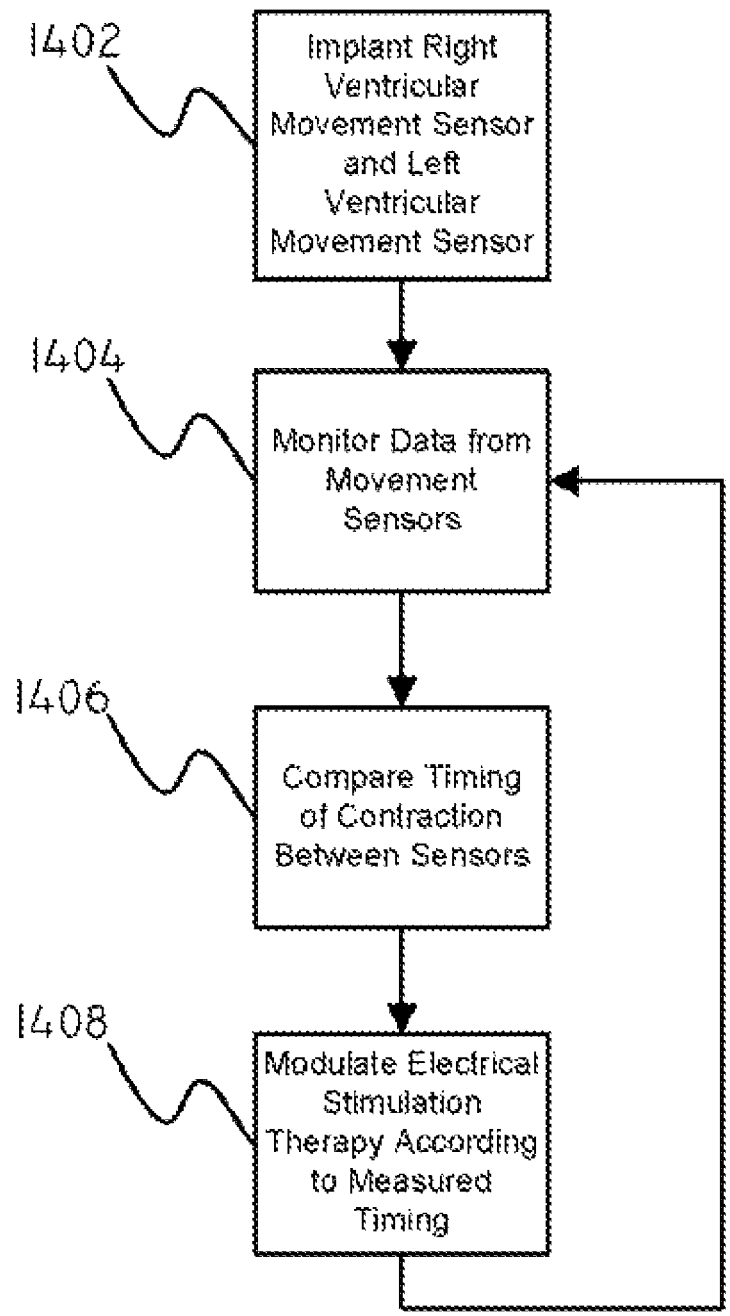
FIG. 17 is a flow chart illustrating operations of a method in accordance with another embodiment of the invention.

Referring now to FIG. 17, a flow chart is shown illustrating a method of monitoring synchrony between contractions of the left and right ventricles. In an embodiment, the invention includes an implantable medical device including a processor, the medical device configured to execute operations of a method of monitoring synchrony between contractions of the left and right ventricles. In a first operation 1402, two or more movement sensors are implanted in a patient so that movement of both the left ventricle and the right ventricle can be monitored. In a second operation 1404, data from both movement sensors is monitored. In a third operation 1406, the timing of contraction of each of the ventricles is compared. In a fourth operation 1408, appropriate therapy is initiated in order to bring the contractions of the right and left ventricles back into synchrony. Appropriate therapy can include initiation and/or modulation of electrical stimulation therapy as provided by a CRM device.

Analysis of movement data can also be useful in order to identify whether hemodynamic issues are caused by abnormalities affecting systole or diastole. By way of example, one cause of reduced cardiac output is a failure of the ventricle to contract fully and with enough force to pump out a sufficient amount of blood (sometime referred to as systolic cardiac dysfunction or systolic heart failure). Another cause of reduced cardiac output is an inadequate amount of blood flowing into the ventricle in between contractions (sometimes referred to as diastolic cardiac dysfunction or diastolic heart failure). A method of differentiating between systolic and diastolic hemodynamic problems can be described as follows. In a first operation, one or more movement sensors are implanted in a patient so that movement of one or both of the left ventricle and the right ventricle can be monitored. In a second operation, the movement data is monitored for abnormalities during systole. For example, various measures such as displacement, curvature, torsion, velocity, and/or acceleration of movement are evaluated during systole, which can be surrogate parameters for cardiac contractility and afterload. In some embodiments, cardiac contractility and afterload are calculated from the movement data during systole. In a third operation, the movement data is monitored for abnormalities during diastole. For example, various measures such as displacement, curvature, torsion, velocity, and/or acceleration of movement are evaluated during diastole, which can be surrogate parameters for cardiac structural compliance, relaxing speed, and preload. In some embodiments, cardiac structural compliance, relaxing speed, and preload are calculated from the movement data during diastole. In a fourth operation, the hemodynamic problem is diagnosed based on comparison of the movement data in systole and in diastole. For example if the magnitude and/or velocity of movement during systole is abnormal, then the problem can be classified as systolic cardiac dysfunction. Alternatively, if the magnitude and/or velocity of movement during diastole is abnormal, then the problem can be classified as diastolic cardiac dysfunction.

One of ordinary skill in the art will understand that the operations and methods shown and described herein with regard to various embodiments of the invention can be implemented using software, hardware, and combinations of software and hardware. As such, the illustrated and/or described operations and methods are intended to encompass software implementations, hardware implementations, and software and hardware implementations.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable electrical stimulation lead comprising:
a lead body having a proximal end and a distal end, the lead body comprising a sheath defining a central lumen, the lead body further comprising an electrical conductor disposed within the central lumen of the sheath;
a stimulation electrode positioned at the distal end of the lead body, the stimulation electrode in electrical communication with the electrical conductor; and
a first flexion sensor coupled to the lead body at a point closer to the distal end than the proximal end, the first flexion sensor configured to generate an electrical signal in response to flexion of the lead body, wherein the first flexion sensor is a helical sensing element.

2. The implantable electrical stimulation lead of claim 1, the first flexion sensor comprising a resistive element that changes electrical resistance in response to flexion.

3. The implantable electrical stimulation lead of claim 2, the resistive element comprising conductive carbon particles.

4. The implantable electrical stimulation lead of claim 2, the resistive element wrapped around the sheath.

5. The implantable electrical stimulation lead of claim 1, the lead body comprising a layer of insulation surrounding the electrical conductor, the first flexion sensor disposed on the layer of insulation.

6. The implantable electrical stimulation lead of claim 1, the sheath having an outside surface, the first flexion sensor disposed on the outside surface.

7. The implantable electrical stimulation lead of claim 1, the sheath having an inner surface, the first flexion sensor disposed on the inner surface of the sheath.

8. The implantable electrical stimulation lead of claim 1, further comprising a second flexion sensor coupled to the lead body.

9. The implantable electrical stimulation lead of claim 8, the second flexion sensor coupled to the lead body at a point between the first flexion sensor and the proximal end of the implantable electrical stimulation lead.

10. The implantable electrical stimulation lead of claim 1, the sheath comprising a biocompatible material.

11. The implantable electrical stimulation lead of claim 10, wherein the biocompatible material is one of polysiloxanes, polyethylenes, and polyamides.

12. The implantable electrical stimulation lead of claim 1, the first flexion sensor comprising a piezoelectric element.

13. The implantable electrical stimulation lead of claim 1, the first flexion sensor comprising a substrate and a conductive material layer disposed over the substrate.

14. The implantable electrical stimulation lead of claim 13, the conductive material layer configured to change in resistance in response to the degree to which the conductive material layer is flexed.

15. The implantable electrical stimulation lead of claim 13, wherein the thickness of the conductive material layer in combination with the substrate is less than about 0.25 mm.

16. The implantable electrical stimulation lead of claim 13, wherein the thickness of the conductive material layer in combination with the substrate is less than about 0.1 mm.

17. The implantable electrical stimulation lead of claim 1, wherein the first flexion sensor is an optical flexion sensor.

18. The implantable electrical stimulation lead of claim 17, the optical flexion sensor comprising an optical fiber with a core surrounded by a cladding layer.

19. The implantable electrical stimulation lead of claim 18, wherein portions of the cladding layer have been removed to enhance sensitivity of the optical fiber to bending signal loss.

20. The implantable electrical stimulation lead of claim 17, the optical flexion sensor comprising a bend-enhanced fiber sensor.

* * * * *